(12) United States Patent
Alexis

(10) Patent No.: US 12,409,319 B2
(45) Date of Patent: Sep. 9, 2025

(54) DEVICE AND METHOD FOR CARDIOTHORACIC SURGERY

(71) Applicant: Sophia L. Alexis, Caldwell, NJ (US)

(72) Inventor: Sophia L. Alexis, Caldwell, NJ (US)

( * ) Notice: Subject to any disclaimer, the term of this patent is extended or adjusted under 35 U.S.C. 154(b) by 0 days.

(21) Appl. No.: 19/058,160

(22) Filed: Feb. 20, 2025

(65) Prior Publication Data

US 2025/0186767 A1   Jun. 12, 2025

(51) Int. Cl.
*A61M 27/00* (2006.01)
*A61N 1/05* (2006.01)

(52) U.S. Cl.
CPC ........... *A61N 1/0597* (2013.01); *A61M 27/00* (2013.01); *A61N 1/0595* (2013.01); *A61M 2210/101* (2013.01)

(58) Field of Classification Search
CPC .. A61N 1/0597; A61N 1/0595; A61N 1/0587; A61N 1/056; A61N 1/3625; A61M 27/00; A61M 2210/101; A61M 2025/0166; A61M 2205/054; A61M 2210/125; A61B 8/12; A61B 17/0057; A61B 8/06; A61B 8/445; A61B 17/00234; A61B 18/1492; A61B 2017/00278; A61B 5/029; A61B 1/00094; A61B 1/00154; A61B 1/015; A61B 1/018; A61B 2017/00243; A61B 2018/00351; A61B 2018/00363; A61B 2218/007

See application file for complete search history.

(56) References Cited

U.S. PATENT DOCUMENTS

| | | | |
|---|---|---|---|
| 6,231,514 B1 * | 5/2001 | Lowe | A61B 8/12 600/462 |
| 8,210,183 B2 | 7/2012 | Zotz | |
| 10,610,208 B2 | 4/2020 | Whayne et al. | |
| 2001/0039415 A1 * | 11/2001 | Francischelli | A61B 5/411 600/549 |
| 2002/0002372 A1 * | 1/2002 | Jahns | A61B 18/1492 604/35 |
| 2002/0019623 A1 * | 2/2002 | Altman | A61M 25/0084 604/20 |
| 2004/0220455 A1 * | 11/2004 | Lowe | A61M 25/0105 600/300 |
| 2005/0102015 A1 * | 5/2005 | Lau | A61F 2/2481 607/129 |

(Continued)

*Primary Examiner* — Adam Marcetich
(74) *Attorney, Agent, or Firm* — Michael J. Feigin, Esq.; Feigin and Fridman LLC

(57) ABSTRACT

A device for use during cardiothoracic surgery around the heart of a patient. The device includes an angled drainage tube including a first portion having a plurality of drainage orifices and a second portion which is angled relative to the first portion. A flexible drainage tube extends from the angled tube and is in fluid communication therewith. A pair of pacing electrodes are disposed on a single aspect of the first portion of the angled drainage tube. The pacing electrodes are adapted to be in contact with the heart muscle for intrinsic rhythm sensing and pacing capability thereof. At least one electrical wire is connected to the pacing electrodes and extends along a portion of the angled drainage tube. The at least one electrical wire is connectable to a pacing box via a cable for powering and controlling the pacing electrodes.

17 Claims, 2 Drawing Sheets

(56) References Cited

U.S. PATENT DOCUMENTS

| | | | |
|---|---|---|---|
| 2006/0100683 A1* | 5/2006 | Yacoubian | A61N 1/0587 607/129 |
| 2008/0046061 A1* | 2/2008 | Yacoubian | A61N 1/0587 607/126 |
| 2008/0051864 A1* | 2/2008 | Callas | A61N 1/059 607/130 |
| 2009/0299447 A1* | 12/2009 | Jensen | A61N 1/0587 607/130 |
| 2010/0114093 A1* | 5/2010 | Mahapatra | A61M 25/0133 606/41 |
| 2011/0034912 A1* | 2/2011 | de Graff | A61N 7/022 606/41 |
| 2011/0071415 A1* | 3/2011 | Karwoski | A61M 25/10 604/319 |
| 2014/0371789 A1 | 12/2014 | Hariton et al. | |
| 2018/0353751 A1* | 12/2018 | Pedersen | A61N 1/056 |
| 2019/0224476 A1* | 7/2019 | Sun | A61N 1/3968 |
| 2022/0118261 A1* | 4/2022 | Pedersen | A61N 1/056 |
| 2022/0379004 A1* | 12/2022 | Hellman | A61M 25/003 |
| 2023/0181882 A1* | 6/2023 | Dowell | A61M 27/00 604/540 |
| 2024/0252817 A1* | 8/2024 | Pedersen | A61N 1/056 |

* cited by examiner

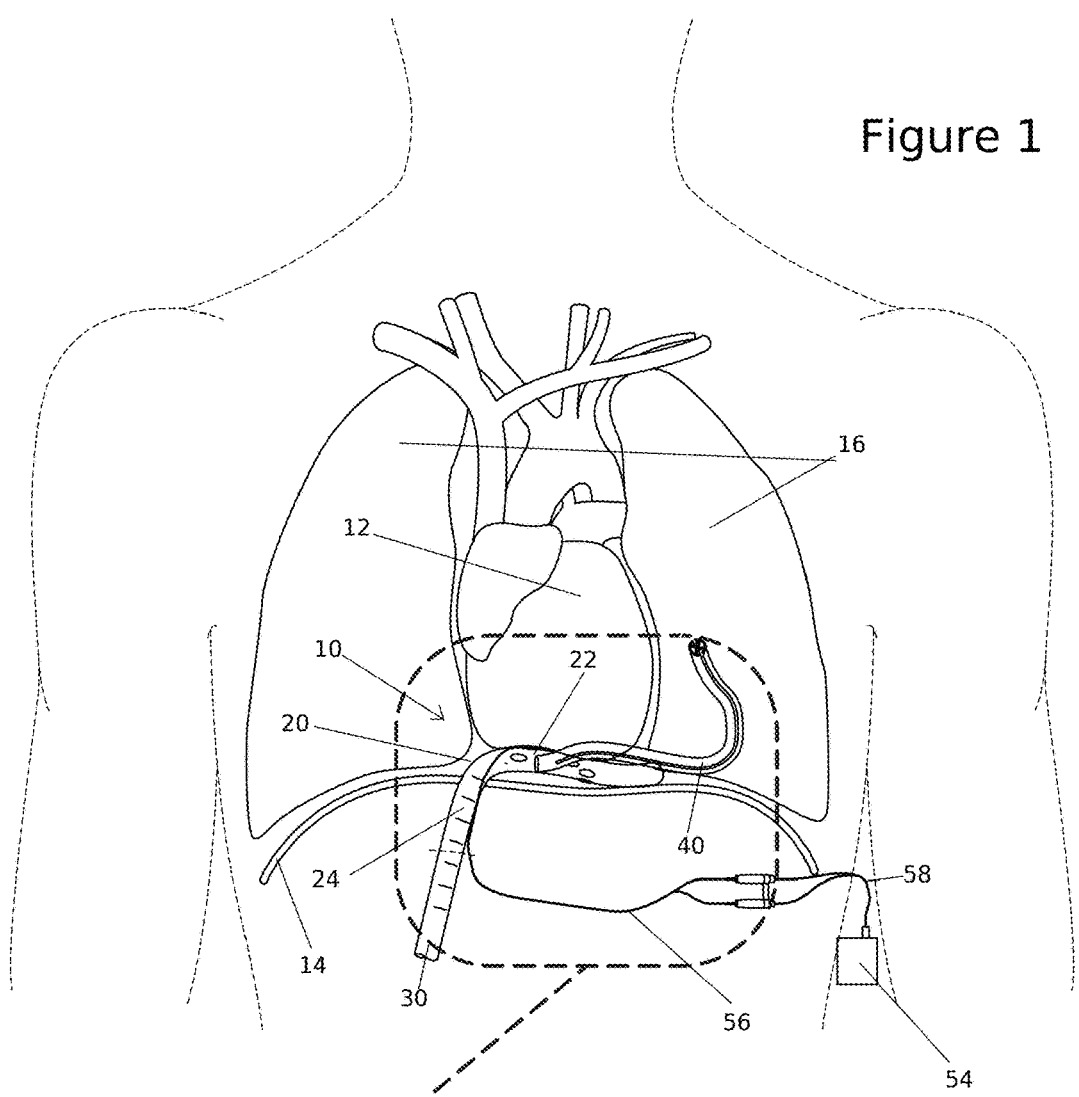
Figure 1
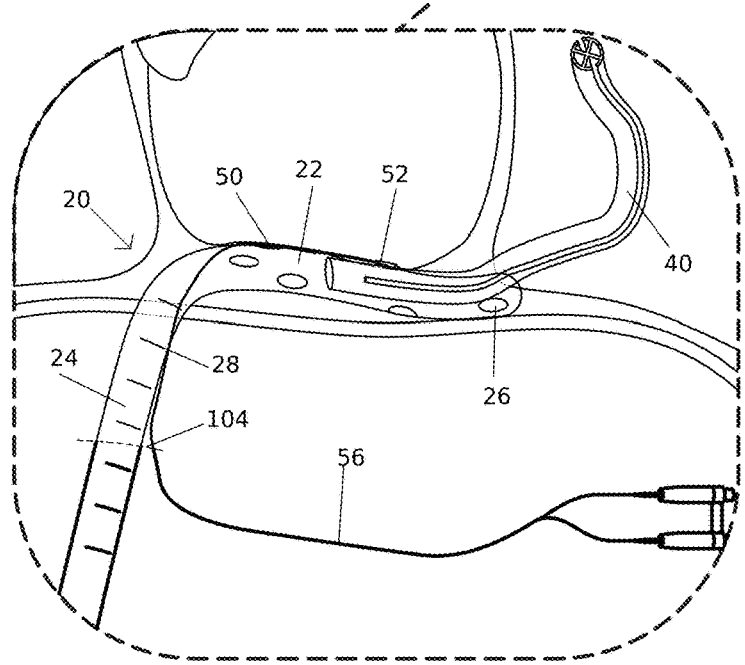

DEVICE AND METHOD FOR CARDIOTHORACIC SURGERY

FIELD OF THE DISCLOSED TECHNOLOGY

The disclosed technology relates generally to devices and methods used during cardiothoracic surgery and, more specifically, to a device and method for draining the mediastinum and/or the pleural space and for sensing and pacing the heart's rhythm perioperatively. The device and method refrain from violating the cardiac tissue and use a single incision for the device to exit the body.

BACKGROUND OF THE DISCLOSED TECHNOLOGY

Since the advent of cardiothoracic surgery, there has been a lack of evolution in the standard required perioperative draining and pacing practices.

Typically, multiple incisions are made in the subxiphoid and subcostal regions for placement of chest drains and one or more pacing wires. While there is a degree of variation in surgeons' preferences, typically a patient post-operatively will have multiple chest tubes connected to one or more drainage boxes and one or more temporary pacing wires that are connected to an external device to help control cardiac electrophysiology. Such use of multiple incisions/products generates a higher chance of infection for the patient, increased pain, and a worse cosmetic result. Furthermore, these practices have unavoidable environmental waste, as the tubes and wire(s) are all single-use, plastic wrapped products that are individually packaged.

Additionally, bipolar pacing wires, which exit the body and connect to an external pacing box, currently require electrodes that are sutured into the heart muscle to ensure proper sensing and pacing of the heart. This process requires violating the epicardium and the myocardium. Furthermore, removal of the pacing wire presents a risk of bleeding, which can lead to severe consequences, including death. Traditional methods of wire removal risk hemopericardium and tamponade and create a clinical conundrum in patients who require anticoagulation, have had difficult wire placement, or are coagulopathic. Avoiding wire removal by cutting of the pacing wire at the skin leaves a retained device within the body, risking migration, damage to nearby structures, and patient discomfort.

There is thus a need in the art for a device and a method suitable for drainage in cardiothoracic surgery, which reduce the number of surgical incisions. There is further a need in the art for a device and a method suitable for sensing and/or pacing the heart after cardiothoracic surgery, without attaching electrodes to the heart muscle. These features will become increasingly important with the continued growth and pursuit of minimally invasive techniques.

SUMMARY OF THE DISCLOSED TECHNOLOGY

The disclosed technology relates generally to devices and methods used during cardiothoracic surgery and, more specifically, to a device and method for draining the mediastinum and/or the pleural space and for sensing and pacing the heart's rhythm perioperatively. The device and method refrain from violating the cardiac tissue and uses a single incision for the device to exit the body.

According to an aspect of some embodiments of the teachings herein, there is provided a device for use during cardiothoracic surgery surrounding the heart of a patient in the pericardial well. The device includes an angled drainage tube. The angled drainage tube includes a first portion having a plurality of drainage orifices and a second portion, which is angled relative to the first portion.

The device further includes a flexible drainage tube, extending from the angled drainage tube and in fluid communication with the angled drainage tube.

The device further includes a pair of pacing electrodes, disposed on a single aspect of the first portion of the angled drainage tube. The pair of pacing electrodes are adapted to contact the ventricular muscle of the heart of the patient for pacing thereof.

The device further includes at least one electrical wire, connected to the pacing electrodes and extending along, or through, at least a portion of the angled drainage tube. The at least one electrical wire is connectable to a standard pacing box via a cable for powering and controlling the pair of pacing electrodes, for example the electrodes' pacing, sensing, and/or impedance.

In some embodiments, the angled drainage tube has a first diameter, and the flexible drainage tube has a second diameter, the second diameter being smaller than the first diameter.

In some embodiments, the angled drainage tube is adapted to be in fluid communication with a drainage box, the drainage box adapted to receive fluid drained by the angled drainage tube and by the flexible drainage tube.

In some embodiments, the angled drainage tube has a first rigidity, and the flexible drainage tube has a second rigidity, smaller than the first rigidity.

In some embodiments, the second portion of the angled tube includes a plurality of distance markers.

In some embodiments, the pair of pacing electrodes form part of a pacing plate, disposed on the single aspect of the first portion of the angled drainage tube, the pacing plate being connected to the at least one wire.

In some embodiments, the at least one wire is, or includes, a bipolar wire.

In some embodiments, the pair of pacing electrodes are adapted to pace the heart muscle of the patient's heart when resting against the heart muscle, without being fixed thereto.

According to an aspect of some embodiments of the teachings herein, there is provided a kit for use during cardiothoracic surgery on the heart of a patient. The kit includes the device as disclosed herein, and a pacing box, connectable to the at least one wire, for example via a cable. The pacing box is adapted to power and control operation of the pair of pacing electrodes for pacing the heart, during operation of the pacing box.

The kit further includes a drainage box, connectable to the angled drainage tube and adapted to be in fluid communication therewith. The drainage box is adapted to receive fluid drained by the angled drainage tube and by the flexible drainage tube.

According to an aspect of some embodiments of the teachings herein, there is provided a method of setting up for cardiothoracic surgery on a patient using the kit disclosed herein. The method includes creating a single incision in the subxiphoid area of the subject. The method further includes inserting the device into the body of the patient via the single incision, and positioning the device such that: (i) the first portion of the angled drainage tube is disposed between the heart muscle and the diaphragm, such that the pair of pacing electrodes are in direct contact with the heart muscle; (ii) the second portion of the angled drainage tube and the at least one wire extend out of the single incision to the exterior of the patient's body; and (iii) the flexible drainage tube is positioned in an additional region to be drained, for example in the mediastinum or pleural space of the patient.

In some embodiments, the method further includes connecting the at least one wire to the pacing box, with the pacing box disposed outside the body of the patient.

In some embodiments, the method further includes connecting the second portion of the angled drainage tube to the drainage box, with the drainage box disposed outside the body of the patient.

In some embodiments, the positioning of the device is such that the pair of pacing electrodes is placed against the heart muscle without being fixed thereto.

According to an aspect of some embodiments of the teachings herein, there is provided a method of conducting cardiothoracic surgery, the method including performing cardiothoracic surgery using the method and kit disclosed herein, activating the pacing box to cause the pair of pacing electrodes to pace the heart of the patient when necessary, and connecting the drainage box to drain fluid from the body of the patient via the angled drainage tube and the flexible drainage tube, during the perioperative period.

In some embodiments, the method further includes, during a post-surgery recovery duration, retaining the angled drainage tube and the flexible drainage tube within the body of the patient, the angled drainage tube and the at least one wire extending out of the single incision, the angled drainage tube being in fluid communication with the drainage box and the pair of pacing electrodes being attached to the pacing box, continuing to sense the intrinsic cardiac rhythm and when necessary pace the heart, and continuing to drain fluid from the mediastinum and/or pleural space.

In some embodiments, the method further includes, following completion of the post-surgery recovery duration, removing the angled drainage tube, the flexible drainage tube, and the at least one wire, from the body of the subject, via the single incision.

According to an aspect of some embodiments of the teachings herein, there is provided a system for use during cardiothoracic surgery around the heart of a patient. The system includes an angled drainage tube including a first portion having a plurality of drainage orifices and a second portion, which is angled relative to the first portion. The system further includes a flexible drainage tube, extending from the angled drainage tube and in fluid communication with the angled drainage tube.

The system can further include a pair of pacing electrodes, disposed on a single aspect of the first portion of the angled drainage tube. The pair of pacing electrodes are adapted to contact the heart muscle for intrinsic sensing and pacing thereof.

The system can further include at least one electrical wire, connected to the pacing electrodes and extending through, or along, at least a portion of the angled drainage tube.

The system can further include a pacing box, connectable, for example via a cable to the at least one wire. The pacing box is adapted to power and control operation of the pair of pacing electrodes for pacing the heart of the subject, during operation of the pacing box. The pacing box is adapted to remain outside the patient's body.

The system can further include a drainage box, connectable to the angled drainage tube and adapted to be in fluid communication therewith. The drainage box is adapted to receive fluid drained by the angled drainage tube and by the flexible drainage tube. The drainage box is adapted to remain outside the patient's body.

In some embodiments, the angled drainage tube has a first diameter, and the flexible drainage tube has a second diameter, the second diameter being smaller than the first diameter.

In some embodiments, the angled drainage tube has a first rigidity, and the flexible drainage tube has a second rigidity, smaller than the first rigidity. For the purposes of the present application and claims, a smaller rigidity corresponds to a softer, or more malleable, material, and a higher rigidity corresponds to a harder, or less malleable, material.

In some embodiments, the second portion of the angled tube includes a plurality of distance markers.

In some embodiments, the pair of pacing electrodes form part of a pacing plate, disposed on the single aspect of the first portion of the angled drainage tube, the pacing plate being connected to the at least one wire.

In some embodiments, the at least one wire comprises a bipolar wire.

In some embodiments, the pair of pacing electrodes are adapted to sense and pace the heart muscle when resting against the heart muscle, without being fixed thereto.

BRIEF DESCRIPTION OF THE DRAWINGS

FIG. 1 is a schematic illustration of a draining and pacing device, according to an embodiment of the disclosed technology, disposed within the body of a subject.

DETAILED DESCRIPTION OF EMBODIMENTS OF THE DISCLOSED TECHNOLOGY

Figure 2:
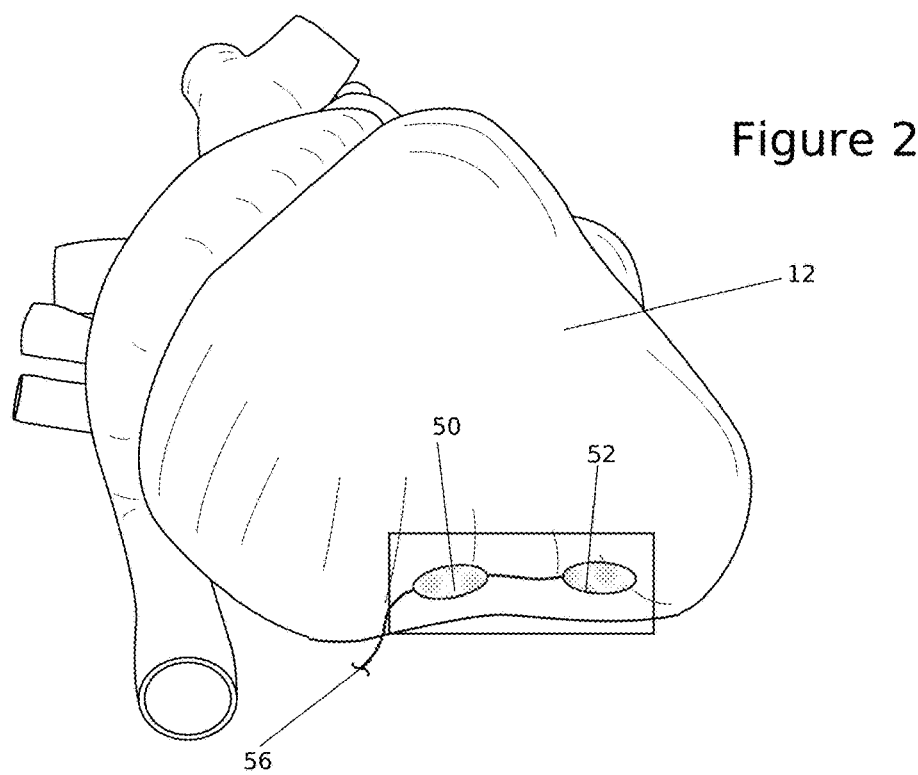
FIG. 2 is a schematic illustration of a pacing plate, forming part of the device of FIG. 1, placed against the heart of a subject, according to an embodiment of the disclosed technology.

In an embodiment of the disclosed technology, a device for use during cardiothoracic surgery includes a right-angle drainage tube having a first portion adapted to be disposed between the heart and the diaphragm, and a second portion disposed at a right angle to the first portion. The first portion of the right-angle drainage tube includes a plurality of drainage ports.

A pair of pacing electrodes are mounted on a single side of the right-angle drainage tube. The pacing electrodes are adapted to engage the base of the heart, and to sense the intrinsic cardiac rhythm/pace the heart when necessary, without being directly attached to the heart muscle. The pacing electrodes are adapted to be out of physical contact from the diaphragm on the contralateral portion of the tube. The pacing electrodes are adapted to be connected to a pacing box, for example via a cable, the wire(s) incorporated into, or on, or through, at least a portion of the right-angle drainage tube.

The device further includes a flexible drainage limb, extending out of the right-angle drainage tube, and adapted to be directed into a separate area of the mediastinum or the pleural space. The device is adapted to exit and extend out of the body of the subject via a single incision in the subxiphoid area of the body.

Embodiments of the disclosed technology will become clearer in view of the following description of the drawings.

Reference is now made to FIG. 1, which shows a schematic illustration of a draining and pacing device 10, according to an embodiment of the disclosed technology, disposed within the body of a subject. The body of the subject includes a heart 12, a diaphragm 14, and lungs 16, such that left and right pleural spaces are disposed around the heart and lungs.

As seen in FIG. 1, the device 10 includes an angled drainage tube 20 which has a first portion 22 and a second portion 24. The second portion 24 is disposed at an angle to the first portion 22, where the angle is approximately a right angle. First portion 22 of tube 20 includes a plurality of drainage orifices 26, and is disposed between heart 12 and diaphragm 14. In some implementations, second portion 24 of tube 20 includes a plurality of distance markers 28, adapted to assist a surgeon in identifying a length of the tube that is from the fenestration nearest to body exit. An end 30 of second portion 24, disposed outside the body of the subject, is adapted to be connected to a drainage box, as known in the art.

For some implementations, angled drainage tube 20 may be a semi-rigid polyvinyl chloride tube. For some implementations, angled drainage tube 20 may be 16 Fr to 40 Fr. For some implementations, angled drainage tube 20 may be a 28 Fr polyvinyl chloride tube.

In some embodiments, a flexible drainage tube 40 extends from angled drainage tube 20. For example, an end of flexible drainage tube 40 may be disposed adjacent to the angle of drainage tube 20. In some embodiments, multiple flexible drainage tubes 40 may be used.

Typically, drainage tube 40 is substantially more flexible than drainage tube 20, and can be oriented, within the body, to drain any desired space or cavity. For example, in the illustrated embodiment, flexible drainage tube 40 is positioned to drain the left pleural space, adjacent to the left lung 16. For some implementations, drainage tube 40 may be a multi-channeled 10 Fr to 24 Fr tube, such as a silicone drain.

In some embodiments, the caliber of drainage tube 40 is smaller than the caliber of angled tube 20. In some embodiments, drainage tube 40 is softer and/or more malleable than angled drainage tube 20 and can be cut to length.

In some other embodiments, drainage tube 40 may be omitted.

Device 10 further includes a pacing component including a positive electrode 50 and a negative electrode 52, connected to a pacing box 54, disposed outside the body, by one or more cables 58. For some implementations, and as shown, a bipolar wire 56 is used within the body, and the wire splits into two components that will connect to the pacing box 54 via one or more cables.

As seen in FIG. 1, electrodes 50 and 52 are disposed on a single aspect of portion 22 of tube 20, which aspect faces and engages the heart 12. Specifically, the electrodes are not circumferential about tube 20. In this manner, the electrodes only impact the heart, and do not impact the diaphragm 14.

As mentioned hereinabove, in the prior art, the electrodes would typically be pierced through or sutured to the heart muscle. This process involves threading a needle through the myocardium. This process is invasive, and can be quite dangerous, particularly because electrode removal can lead to extensive bleeding, hemopericardium, and even death.

When using the device of the disclosed technology, electrodes 50 and 52 remain in place against the base of the heart, without breaching the heart muscle or risking the chance of deleterious bleeding. The placement of electrodes 50 and 52 on the heart, when using device 10 of the disclosed technology, is illustrated in FIG. 2. In FIG. 2, portions of device 10 other than electrodes 50 and 52 are not shown, to clarify the placement of the electrodes against the heart muscle, and to demonstrate that the electrodes engage the base of the ventricle, in a similar manner to that which occurs in the prior art, without being sutured to the heart.

Electrodes 50 and 52 engage an exterior surface of the heart muscle for sensing the heart's intrinsic rhythm and pacing the heart when necessary. As discussed, it is a particular feature of the disclosed technology that the electrodes need not be affixed to the heart muscle. It is to be appreciated that the electrodes are merely in contact with, or placed directly, against the heart muscle, without being in violation of the heart muscle. The electrodes are held in place by proper placement of tube 20.

In some implementations, electrodes 50 and 52 may form part of a conductive (e.g., metallic) plate disposed on the aspect of portion 22 of tube 20.

In some implementations, at least a portion of wire(s) 56, connecting electrodes 50 and 52 with pacing box 54, extend through, along, or on angled drainage tube 20.

Figure 3:
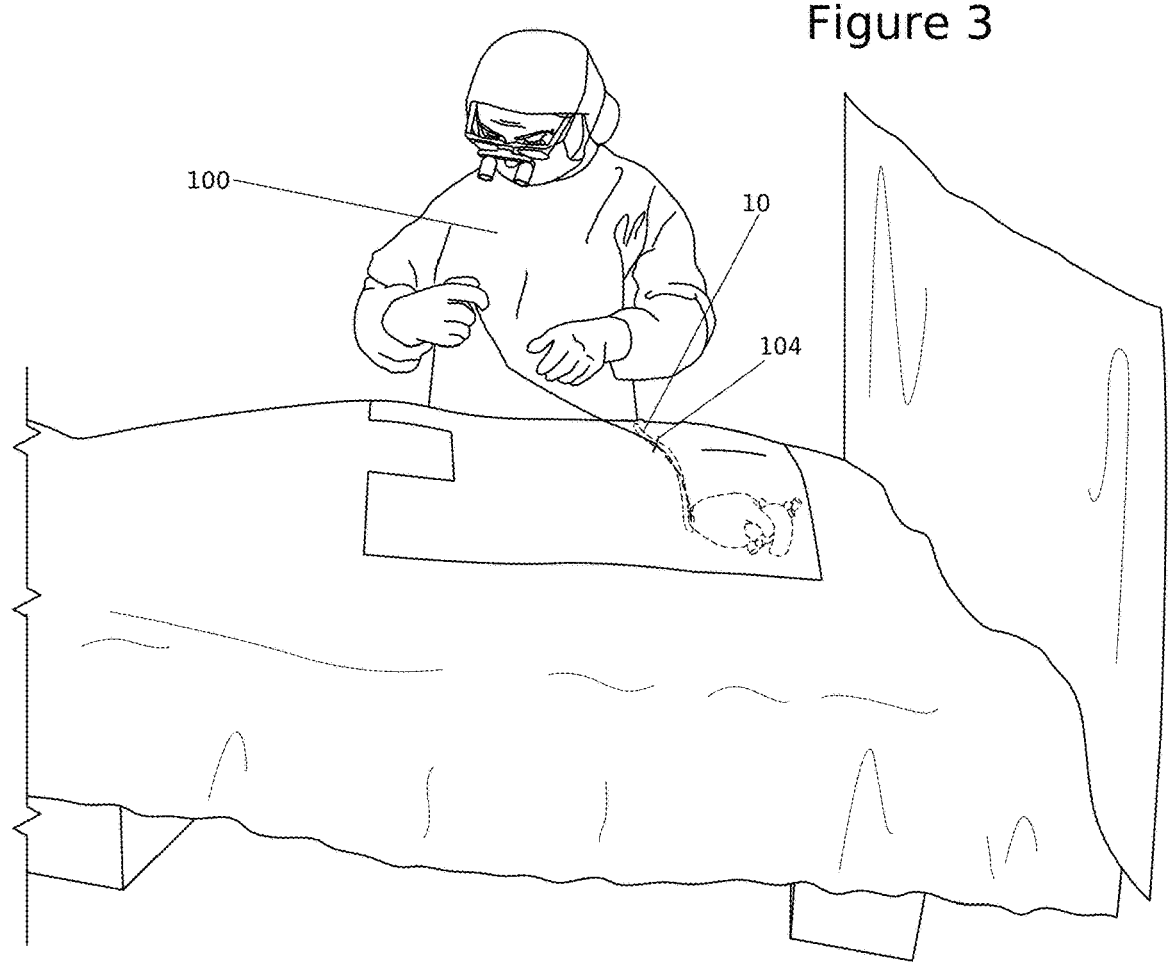
FIG. 3 is a schematic illustration of cardiothoracic surgery conducted using the draining and pacing device of FIG. 1, according to an embodiment of the disclosed technology.

Reference is now additionally made to FIG. 3, which is a schematic illustration of cardiothoracic surgery conducted using a draining and pacing device 10, according to an embodiment of the disclosed technology.

As seen in FIG. 3, a surgeon 100 conducting cardiothoracic surgery on a patient creates a single incision 104 (shown also in FIG. 1) in the subxiphoid region of the patient's body, and the device 10 exits the patient's body via the incision 104. The surgeon positions device 10 as shown in FIG. 1, with angled tube 20 disposed such that electrodes 50 and 52 engage the heart muscle of the patient, and flexible tube 40 drains a desired region, such as a separate area of the mediastinum or the right or left pleural space. The surgeon also connects the angled tube 20 to a drainage box (not explicitly shown) and connects wire(s) 56 to pacing box 54, disposed outside the body of the user.

In the perioperative period, electrodes 50 and 52 will have electrical pacing, sensing, and impedance capabilities, while tubes 20 and 40 drain fluids from the mediastinum and/or pleural space. With these aspects in place, the surgeon can conduct the cardiothoracic surgery as known in the art, the exact actions of the surgeon dependent on the type of cardiothoracic surgery being conducted.

During a post-surgery recovery duration, device 10 remains within the body of the patient, connected to the drainage box and the pacing box, for tubes 20 and 40 to continue draining the mediastinum and/or pleural space and for electrodes 50 and 52 to continue sensing and pacing the heart when necessary. However, the use of a single incision for device 10 placement from the body of the patient, ensures that the patient only has a single incision with devices exiting their body during this post-surgery recovery duration. This significantly reduces the risk of infection for the patient, decreases pain, and improves cosmetic result. It is also more environmentally friendly to have one comprehensive device.

Because electrodes 50 and 52 are not sutured to the heart muscle, but rather are just abutting the heart muscle in engagement therewith, at the end of the post-surgery recovery duration, device 10 can be simply removed from the body of the patient via incision 104, without injuring the heart, therefore eliminating the risk of bleeding.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

"Substantially" and "substantially shown," for purposes of this specification, are defined as "between and including 90% to 100%," or as otherwise indicated. "Identical" or "exactly," for purposes of this specification, is defined as "within an acceptable tolerance level known in the art." Any device may "comprise," or "consist of," the devices mentioned there-in, as limited by the claims. Any element described may be one of "exactly" or "substantially," as described.

It should be understood that the use of "and/or" is defined inclusively, such that the term "a and/or b" should be read to include the sets: "a and b," "a or b," "a," or "b."

The invention claimed is:

1. A device for use during cardiothoracic surgery on the heart of a patient, the device comprising:
   an angled drainage tube including a first portion having a plurality of drainage orifices and a second portion, the second portion being angled relative to the first portion;
   a pair of pacing electrodes, disposed on a single external surface of the first portion of the angled drainage tube, wherein the electrodes are both oriented towards the heart, the pair of pacing electrodes adapted to rest against the heart muscle of the patient, without breaching the heart muscle and without being sutured, and to contact the heart muscle for sensing an intrinsic rhythm of the heart and/or pacing thereof; and
   at least one electrical wire, connected to the pacing electrodes and extending along at least a portion of the angled drainage tube, the at least one electrical wire being connectable to a pacing box for powering and controlling the pair of pacing electrodes.

2. The device of claim 1, further comprising a flexible drainage tube, extending from the angled drainage tube and in fluid communication with the angled drainage tube.

3. The device of claim 2, wherein
   the angled drainage tube has a first rigidity, and the flexible drainage tube has a second rigidity, smaller than the first rigidity.

4. The device of claim 1, wherein the angled drainage tube is adapted to be in fluid communication with a drainage box, the drainage box adapted to receive fluid drained through the angled drainage tube.

5. The device of claim 1, wherein the pair of pacing electrodes form part of a pacing plate, disposed on the single aspect of the first portion of the angled drainage tube, the pacing plate being connected to the at least one wire.

6. The device of claim 1, wherein the at least one wire comprises a bipolar wire.

7. A kit for use during cardiothoracic surgery around the heart of a patient, the kit including:
   the device of claim 1;
   a pacing box, connectable to the at least one wire, the pacing box adapted to power and control operation of the pair of pacing electrodes for sensing and/or pacing the heart of the subject, during operation of the pacing box; and
   a drainage box, connectable to the angled drainage tube and adapted to be in fluid communication therewith, the drainage box adapted to receive fluid drained through the angled drainage tube.

8. The kit of claim 7, wherein the device further comprises a flexible drainage tube, extending from the angled drainage tube and in fluid communication with the angled drainage tube.

9. A method of setting up for cardiothoracic surgery on the heart of a patient using the kit of claim 8, the method comprising:
   (a) creating a single incision in the subxiphoid area of the body of the subject;
   (b) inserting a portion of the device into the body of the patient via the single incision, such that:
      the first portion of the angled drainage tube is disposed between the heart muscle and the diaphragm, such that the pair of pacing electrodes are in direct contact with the heart muscle, without breaching the heart muscle or being sutured; and
      the second portion of the angled drainage tube and the at least one wire extend through the single incision to the exterior of the patient's body;
   (c) connecting the at least one wire to the pacing box, with the pacing box disposed outside the body of the patient; and
   (d) connecting the second portion of the angled drainage tube to the drainage box, with the drainage box disposed outside the body of the patient.

10. A method of conducting cardiothoracic surgery on the heart of a patient, the method comprising:
    (a) setting up for cardiothoracic surgery using the method of claim 9;
    (b) activating the pacing box to cause the pair of pacing electrodes to sense and/or pace the heart of the patient;
    (c) connecting the drainage box to drain fluid from the body of the patient via the angled drainage tube; and
    (d) while the heart of the patient is being sensed and/or paced and the fluid from the body is being drained, managing the perioperative cardiothoracic period.

11. The method of claim 10, further comprising, during a post-surgery recovery duration:
    (e) retaining the angled drainage tube within the body of the patient, the angled drainage tube and the at least one wire extending out of the single incision, the angled drainage tube being in fluid communication with the drainage box and the pair of pacing electrodes being attached to the pacing box;
    (f) continuing to sense and/or pace the heart of the patient, when necessary; and
    (g) continuing to drain fluid from the vicinity of the heart of the patient.

12. The method of claim 11, further comprising, following completion of the post-surgery recovery duration:
    (h) removing the angled drainage tube and the at least one wire, from the body of the subject, via the single incision, without breaching the heart muscle.

13. A system for use during cardiothoracic surgery, the system comprising:
    an angled drainage tube including a first portion having a plurality of drainage orifices and a second portion, the second portion being angled relative to the first portion;
    a flexible drainage tube, extending from the angled drainage tube and in fluid communication with the angled drainage tube;
    a pair of pacing electrodes, disposed on a single external surface of the first portion of the angled drainage tube, wherein the electrodes are both oriented towards the heart, the pair of pacing electrodes adapted to rest against the base of the heart of the patient, without breaching the heart muscle and without being sutured, and to contact the heart muscle for sensing and/or pacing thereof;

at least one electrical wire, connected to the pacing electrodes and extending along at least a portion of the angled drainage tube;

a pacing box, connectable to the at least one wire, the pacing box adapted to power and control operation of the pair of pacing electrodes for pacing the heart of the subject, during operation of the pacing box, and adapted to remain outside the patient's body; and a drainage box, connectable to the angled drainage tube and adapted to be in fluid communication therewith, the drainage box adapted to receive fluid drained by the angled drainage tube and by the flexible drainage tube, and adapted to remain outside the patient's body.

14. The system of claim 13, wherein the angled drainage tube has a first diameter, and the flexible drainage tube has a second diameter, the second diameter being smaller than the first diameter.

15. The system of claim 13, wherein the angled drainage tube has a first rigidity, and the flexible drainage tube has a second rigidity, smaller than the first rigidity.

16. The system of claim 13, wherein the pair of pacing electrodes form part of a pacing plate, disposed on the single aspect of the first portion of the angled drainage tube, the pacing plate being connected to the at least one wire.

17. The system of claim 13, wherein the at least one wire comprises a bipolar wire.

* * * * *